United States Patent [19]

Yamabe et al.

[11] 4,318,867
[45] Mar. 9, 1982

[54] PROCESS FOR PRODUCING DIFLUOROIODOACETYL FLUORIDE

[75] Inventors: Masaaki Yamabe, Machida; Seiji Munekata, Tokyo; Seisaku Kumai, Yokohama, all of Japan

[73] Assignee: Asahi Glass Company, Ltd., Tokyo, Japan

[21] Appl. No.: 150,919

[22] Filed: May 19, 1980

[30] Foreign Application Priority Data

Jun. 12, 1979 [JP] Japan .................................. 54-73020

[51] Int. Cl.$^3$ ............................................. C07C 51/58
[52] U.S. Cl. .............................. 260/544 F; 260/456 R
[58] Field of Search ........................ 260/456 R, 544 F

[56] References Cited

U.S. PATENT DOCUMENTS

| 3,231,626 | 1/1966 | Hauptschein et al. | 260/456 F |
|---|---|---|---|
| 3,311,658 | 3/1967 | Warnell | 260/544 F |
| 3,348,419 | 4/1966 | Hauptschein et al. | 260/456 F |
| 4,116,977 | 9/1978 | Yamabe et al. | 260/343.6 |

FOREIGN PATENT DOCUMENTS 52-111011 3/1977 Japan .

Primary Examiner—Natalie Trousof
Assistant Examiner—L. Hendriksen
Attorney, Agent, or Firm—Oblon, Fisher, Spivak, McClelland & Maier

[57] ABSTRACT

A process for producing difluoroiodoacetyl fluoride comprises a step of producing an intermediate having a group of $ICF_2CF_2OSO_2-$ by reacting 1,2-diiodotetrafluoroethane with an oxidizing acid having S(VI) atom and a step of decomposing said intermediate into said product.

9 Claims, No Drawings

PROCESS FOR PRODUCING DIFLUOROIODOACETYL FLUORIDE

BACKGROUND OF THE INVENTION

1. Field of the Invention

The present invention relates to a process for producing difluoroiodoacetyl fluoride having high purity in high yield.

2. Description of the Prior Art

Difluoroiodoacetyl fluoride ($ICF_2COF$) is useful as the intermediate for various fluorinated compounds or a compound having special characteristics.

For example, difluoroiodoacetyl fluoride can be converted into $\omega$-iodoperfluorocarbon vinyl ether which is useful as a source for thermosetting fluorinated resins, by reacting it with hexafluoropropylene oxide and thermally decomposing the product. Difluoroiodoacetyl fluoride can be converted into perfluorosuccinyl fluoride by a deiodocoupling. The resulting perfluorosuccinyl fluoride can be converted into perfluorodicarboxylic acid derivatives which are useful as sources for fluorinated polycondensates such as polyamides and polyesters having excellent heat resistance and chemical stability, by reacting it with a nucleophilic reagent. Difluoroiodoacetyl fluoride can be used as a source for oxalyl fluoride which is useful as an intermediate for various fluorinated compounds.

Heretofore, it has been known to produce difluoroiodoacetyl fluoride by reacting anhydrous lithium chloride with tetrafluoroethylene oxide in acetyl anhydride (U.S. Pat. No. 3,311,658). In this known process, it is indispensable to use tetrafluoroethylene oxide which is not easily produced in view of an explosive reaction and a low yield. Moreover, the yield of difluoroiodoacetyl fluoride is only less than 40% based on tetrafluoroethylene oxide. Therefore, this process is not satisfactory as an industrial process.

On the other hand, the inventors have studied series of reactions of $\alpha,\omega$-diiodopolyfluoroalkane with an oxidizing acid. As a result, it has been found that when $\alpha,\omega$-diiodopolyfluoroalkane having carbon atoms of 6 or more is used fluorinated diacid fluorides are mainly obtained; and when $\alpha,\omega$-diiodopolyfluoroalkane having carbon atoms of 3 to 5 is used, cyclic compounds such as fluorinated lactones and fluorinated cyclic ethers are obtained and when $\alpha,\omega$-diiodoalkane having carbon atoms of 3 to 5 are reacted with fuming sulfuric acid, a ratio of the production of the fluorinated cyclic ether is increased depending upon increase of a concentration of sulfur trioxide, whereas a ratio of the production of fluorinated lactone is increased depending upon decrease of a concentration of sulfur trioxide. (U.S. Pat. No. 4,116,977 and Japanese Unexamined Publication No. 111011/1978).

The present invention has been accomplished by the following novel surprising findings in the series of studies.

SUMMARY OF THE INVENTION

It is an object of the present invention to produce difluoroiodoacetyl fluoride in high yield without any dangerous step.

The foregoing and other objects of the present invention have been attained by producing difluoroiodoacetyl fluoride by (a) a step of producing an intermediate having a group of $ICF_2CF_2OSO_2-$ by reacting 1,2-diiodotetrafluoroethane with an oxidizing acid having a hexavalent sulfur atom, hereinafter referred to as S(VI) atom and (b) a step of decomposing the intermediate into the product.

The intermediate can be one or more compounds having a group of $ICF_2CF_2OSO_2-$.

DETAILED DESCRIPTION OF THE PREFERRED EMBODIMENTS

The reaction of 1,2-diiodotetrafluoroethane with an oxidizing acid having S(VI) atom is remarkably different from the oxidation of $\alpha,\omega$-diiodoalkane having carbon atoms of 3 or more. The stable intermediate having a group of $ICF_2CF_2OSO_2-$ as a partially oxidized product is produced in high yield. Difluoroiodoacetyl fluoride is produced in high yield by a decomposition of the intermediate.

In the process of the present invention, it is important to use 1,2-diiodotetrafluoroethane as a reagent and to use an oxidizing acid having S(VI) atom as an oxidizing agent. In accordance with this combination, the intermediate having a group of $ICF_2CF_2SO_2-$ which is converted into difluoroiodoacetyl fluoride, can be obtained in high yield. Therefore, difluoroiodoacetyl fluoride can be produced in high yield from 1,2-diiodotetrafluoroethane.

The oxidizing agents or acids having S(VI) atom can be sulfur trioxide, fuming sulfuric acid and halosulfonic acids such as fluorosulfonic acid and chlorosulfonic acid. In view of an easy separation of the intermediate and a reactivity, it is preferable to use sulfur trioxide.

A ratio of the oxidizing acid to 1,2-diiodotetrafluoroethane is not critical and is depending upon a kind of an oxidizing acid and a condition for the reaction. For example, when sulfur trioxide is used as the oxidizing acid, it is confirmed to obtain the partially oxidized intermediate in high yield even though a molar ratio of sulfur trioxide to 1,2-diiodotetrafluoroethane is two or more. It is preferable to be a molar ratio of sulfur trioxide to 1,2-diiodotetrafluoroethane of 0.2 to 5 in view of an efficiency of a reactor and an easy post-treatment.

When fuming sulfuric acid or fluorosulfonic acid is used as the oxidizing acid, a ratio of the oxidizing acid to 1,2-diiodotetrafluoroethane is usually in a range of 0.3 to 3.

The condition of the oxidation is selected depending upon the kind of the oxidizing acid. For example, when sulfur trioxide is used as the oxidizing acid, it is preferable to select at a temperature ranging from $-10°$ to $+120°$ C. When the temperature is too low, the reaction velocity is remarkably low whereas when it is too high, the selectivity to the partially oxidized intermediate is low. These are disadvantageous. When fuming sulfuric acid or fluorosulfonic acid is used as the oxidizing acid, it is preferable to choose a temperature ranging from $30°$ to $150°$ C.

The structure of the intermediate having a group of $ICF_2CF_2OSO_2-$ is dependent upon the kind of the oxidizing agent. When fuming acid or fluorosulfonic acid is used as the oxidizing acid, the intermediate is obtained in a form of $ICF_2CF_2OSO_2F$ [perfluoro(2-iodoethanefluorosulfate)]. When chlorosulfonic acid is used as the oxidizing acid, the intermediate is obtained in a form of $ICF_2CF_2OSO_2Cl$. When sulfur trioxide is used, the intermediate can be isolated in a form of a mixture.

According to an NMR spectrum analysis, it is confirmed that the mixture in the latter case comprises at least four kinds of intermediates. The intermediates as the mixture can be used in the decomposing step and they are decomposed into difluoroiodoacetyl fluoride as the object product.

In the process of the present invention, the decomposition of the intermediate can be performed only by heating it; for example, difluoroiodoacetyl fluoride can be obtained in the yield of 40 to 50% only by heating it at 150° to 200° C. The yield can be increased by using an accelerator for the decomposition.

Various accelerators can be used. Suitable accelerators include alkali metal halides, ammonium halides and quaternary ammonium halides, silver fluoride, and alkali metal perfluoroalkoxides. It is preferable to use alkali metal halides such as potassium fluoride in view of a required content, an activity and an availability.

It is preferable to carry out the decomposing reaction in an aprotic polar solvent in view of an increase of the activity of the accelerator, and an increase of the yield of difluoroiodoacetyl fluoride. Suitable solvents include sulfolane, diglyme, tetraglyme, dioxane, 1,2-dimethoxyethane and tetrahydrofuran. A ratio of the solvent to the intermediate is in a range of 1 to 20 by weight. Difluoroiodoacetyl fluoride is hydrolyzed into difluoroiodoacetic acid ($ICF_2COOH$). It is preferable to carry out the decomposing reaction in the substantial absence of water in view of high yield.

In accordance with the process of the present invention, 1,2-diiodotetrafluoroethane which is stoichiometrically produced by reacting iodine with tetrafluoroethylene, is converted into the intermediate by reacting it with an oxidizing acid and the intermediate is decomposed whereby difluoroiodoacetyl fluoride useful as the intermediate for various fluorinated compounds can be obtained in remarkably high yield. This is remarkably advantageous in an industrial process.

The present invention will be illustrated by certain examples and references which are provided for purposes of illustration only and are not intended to be limiting the present invention.

EXAMPLE 1

In a four necked flask equipped with a thermometer, a dropping funnel, a stirrer and a refluxing condenser connecting a trap kept at a dry ice temperature at its top outlet, 307 g. of 1,2-diiodotetrafluoroethane was charged and 155 g. of sulfur trioxide was added dropwise during 4 hours through a dropping funnel in a nitrogen atmosphere with thoroughly stirring at a reaction temperature of 5° to 20° C.

After the addition, a precipitation of iodine was found at the bottom and 26 g. of sulfur dioxide was collected in the trap. The precipitate of iodine was separated by a filtration of the reaction mixture to obtain 288 g. of the filtrate. According to a gas chromatography analysis and a $^{19}F$-NMR analysis, it was confirmed that a conversion of 1,2-diiodotetrafluoroethane was 94% and a selectivity to the intermediate having a group of $ICF_2CF_2OSO_2$— was 88% and a selectivity to the by-product having a group —$OCF_2CF_2O$— (both C-I bonds are oxidized) was 12%.

Chemical shifts of F atoms in the difluoromethylene groups of the intermediate having a group of $ICF_2CF_2OSO_2$— or the by-product having a group of —$OCF_2CF_2O$— in $^{19}F$-NMB (based on trichlorofluoromethane) and couplings are as follows.

| (a) (b)<br>$ICF_2CF_2OSO_2$—<br>(c)<br>—$OCF_2CF_2O$— | : (a) −65.3 ppm: triplet<br>: (b) −83.8 ~ −85.2 ppm: triplet (four kinds)<br>: (c) −85.6 ppm: singlet |
|---|---|

In a four necked flask equipped with a thermometer, a dropping funnel, a stirrer and a refluxing condenser connected to a trap at a dry ice temperature and a trap at a liquid nitrogen temperature, 80 ml. of sulfolane dried with molecular sieve and 8.0 g. of potassium fluoride dried at 450° C. for 4 hours were charged and vigorously stirred and 29.5 g. of the filtrate obtained in the former step was added dropwise through the dropping funnel at a reaction temperature of 30° to 36° C.

After the addition, the stirring was continued further for 1 hour and the reaction mixture was heated to 46° C. and the products were collected under a reduced pressure in the two traps. A total amount of the collected products was 22.8 g. which contained 16.0 g. of difluoroiodoacetyl fluoride (yield: 80% based on 1,2-diiodotetrafluoroethane) and 0.4 g. of oxalyl fluoride.

EXAMPLE 2

In accordance with the process of Example 1 except using 29.8 g. of the filtrate for the dropwise addition and using diglyme as the aprotic polar solvent in the decomposing reaction at a reaction temperature of 25° to 40° C., the reactions were carried out whereby 12.9 g. of difluoroiodoacetyl fluoride (yield of 64% based on 1,2-diiodotetrafluoroethane) and 0.4 g. of oxalyl fluoride as a by-product were obtained.

EXAMPLE 3

In accordance with the process of Example 1 except using 400 g. of 1,2-diiodotetrafluoroethane and 137.4 g. of sulfur trioxide, the oxidation reaction was carried out. A conversion of 1,2-diiodotetrafluoroethane was 64%, a selectivity to the intermediate having a group of $ICF_2CF_2OSO_2$— was 92.3% and a selectivity to the compound having a group of —$OCF_2CF_2O$— was 7.7%.

The reaction mixture was filtered to separate iodine and the filtrate was decomposed by the process of Example 1 whereby difluoroiodoacetyl fluoride was obtained in the yield of 55% based on 1,2-diiodotetrafluoroethane.

EXAMPLE 4

In a 300 ml. glass flask equipped with a thermometer, a stirrer and an outlet connecting to a trap at a dry ice temperature, 152 g. of 1,2-diiodotetrafluoroethane and 151 g. of 25% fuming sulfuric acid were charged and heated with stirring for 30 minutes in an oil bath at 90° C. and then the reaction temperature was raised to 140° C. during 1 hour, whereby 107 g. of the product was collected in the trap. According to a gas chromatogrum analysis and a $^{19}F$-NMR analysis, it was confirmed that the collected mixture contained 81.1 g. of perfluoro(2-iodoethanefluorosulfonate), 6.3 g. of difluoroiodoacetyl fluoride, 16.3 g. of 1,2-diiodotetrafluoroethane and a small amount of oxalyl fluoride.

The collected mixture was distilled through a column packed with helipack to isolate perfluoro(2-iodoethanefluorosulfate) having a purity of higher than 99%.

Chemical shifts of F atoms of the fluorosulfate in $^{19}$F-NMR (based on trichlorofluoromethane) and couplings are as follows.

| | (a) (b) (c)<br>$ICF_2CF_2OSO_2F$ | |
|---|---|---|
| | Chemical shift | Coupling |
| (a) | −65.5 ppm | triplet |
| (b) | −85.3 ppm | double, triplet |
| (c) | +45.9 ppm | triplet |

Chemical shifts of C atoms in $^{13}$C—NMR (based on tetramethylsilane) are as follows.

| | (d) (e)<br>$ICF_2CF_2OSO_2F$ |
|---|---|
| | Chemical shift |
| (d) | 88.5 ppm |
| (e) | 116.4 ppm. |

According to IR spectrum analysis, it was observed to have the characteristic absorption band of $\nu SO_2$ in $SO_2F$ group at 1490 cm$^{-1}$.

In the reactor of Example 1 used in the second step, 100 ml. of sulfolane dried by molecular sieve and 4.0 g. of dried potassium fluoride were charged and vigorously stirred and 25.0 g. of the isolated fluorosulfate was added dropwise through the dropping funnel during 30 minutes at a reaction temperature of 30° to 40° C. After the addition, the stirring was continued for 5 hours and the product was collected under a reduced pressure. The collected product contained 14.6 g. of difluoroiodoacetyl fluoride.

EXAMPLE 5

In a 500 ml. autoclave made of Hastelloy equipped with a thermometer, a dropping funnel and a stirrer, 177 g. of 1,2-diiodotetrafluoroethane was charged and stirred at 70° C. and 75 g. of fluorosulfonic acid was added dropwise during 1 hour through the dropping funnel. After the addition, the stirring was continued for 2 hours and the product was collected under a reduced pressure. The collected product contained 99.0 g. of perfluoro (2-iodoethanefluorosulfate) and 33.6 g. of the unreacted 1,2 diiodotetrafluoroethane. The fluorosulfate was isolated from the collected product by the process of Example 4. The isolated fluorosulfate was decomposed by the process of Example 4 whereby difluoroiodoacetyl fluoride was obtained in the yield of 85% (based on the fluorosulfate).

I claim:

1. A process for producing difluoroiodoacetyl fluoride which comprises a step of producing an intermediate having a group of $ICF_2CF_2OSO_2$- by reacting 1,2-diiodotetrafluoroethane with an oxidizing acid or agent having an S(VI) atom and selected from the group consisting of sulfur trioxide, fuming sulfuric acid, fluorosulfonic acid and chlorosulfonic acid, and a step of decomposing said intermediate into said product.

2. The process according to claim 1 wherein sulfur trioxide is used at a molar ratio of 0.2 to 5 based on 1,2-diiodotetrafluoroethane.

3. The process according to claim 1 wherein said reaction of sulfur trioxide to 1,2-diiodotetrafluoroethane is carried out at −10° to +120° C.

4. The process according to claim 1 wherein said decomposition of said intermediate is carried out in the presence of an accelerator for decomposition.

5. The process according to claim 4 wherein an alkali metal halide is used as said accelerator.

6. The process according to claim 5 wherein said decomposition of said intermediate is carried out in an aprotic polar solvent.

7. The process according to claim 1 wherein said decomposition of said intermediate is carried out in the substantial absence of water.

8. The process according to claim 6 wherein said decomposition of said intermediate is carried out at 0° to 100° C.

9. The process according to claim 4 wherein said accelerator is added at a molar ratio of 0.1 to 10 based on said intermediate.

* * * * *